United States Patent [19]
Halgren et al.

[11] Patent Number: 5,744,092
[45] Date of Patent: Apr. 28, 1998

[54] AXIALLY MOVABLE CLUSTER CONDUITS FOR PLASTIC PROCESSING IN A SCREW MACHINE

[76] Inventors: Donald N. Halgren, 35 Central St.;
Desider G. Csongor, 19 Bennett St.,
both of Manchester, Mass. 01944

[21] Appl. No.: 773,875

[22] Filed: Dec. 30, 1996

Related U.S. Application Data

[63] Continuation-in-part of Ser. No. 511,055, Aug. 3, 1995, Pat. No. 5,670,112, and a continuation-in-part of Ser. No. 393,200, Feb. 23, 1995, abandoned.

[51] Int. Cl.$^6$ ................................. B29C 45/00
[52] U.S. Cl. .............. 264/572; 264/45.1; 264/241; 264/255; 264/272.11; 264/272.18; 264/279; 264/171.13; 264/171.14; 425/113; 425/131.1; 425/133.1; 425/130; 425/379.1; 425/381
[58] Field of Search ................. 264/45.1, 50, 171.13, 264/171.14, 241, 255, 572, DIG. 14, DIG. 50, 272.11, 272.18, 279; 425/113, 130, 131.1, 133.1, 376.1, 378.1, 379.1, 381, 382 R

[56] References Cited

U.S. PATENT DOCUMENTS

| | | | |
|---|---|---|---|
| 3,387,331 | 6/1968 | Billings | 425/379.1 |
| 3,566,753 | 3/1971 | Mantke | 264/241 |
| 3,694,424 | 9/1972 | Hunkar et al. | 264/526 |
| 4,174,935 | 11/1979 | Driskill | 264/279 |
| 4,302,409 | 11/1981 | Miller et al. | 264/50 |
| 4,770,624 | 9/1988 | Ziegler | 264/209.8 |
| 4,859,068 | 8/1989 | Sironi | 425/130 |
| 5,064,364 | 11/1991 | Muller-Erwig | 425/381 |
| 5,078,948 | 1/1992 | Troutman | 264/526 |
| 5,098,267 | 3/1992 | Cheng | 264/50 |

*Primary Examiner*—Catherine Timm
*Attorney, Agent, or Firm*—Don Halgren

[57] ABSTRACT

The invention comprises a plasticating machine for the working and forcing of plastic material into a mold, said machine including an elongated housing having a first or proximal end and a second or distal end, an elongated screw shaft with a screw flight therearound, the screw shaft being rotatably supported in the elongated housing, for the working of plastic between the screw shaft and the elongated housing with at least one delivery conduit generally longitudinally arranged through the screw shaft, from a proximal end to a distal tip end thereof. The conduit may be arranged to be movable with respect to the screw shaft to permit delivery of a medium through the screw shaft to any plastic being driven from the machine. The medium may be any single or combination of components selected from the group comprising vapor, liquid, gas, powder or solid, to control the machine or treat any plastic being driven therefrom.

3 Claims, 2 Drawing Sheets

AXIALLY MOVABLE CLUSTER CONDUITS FOR PLASTIC PROCESSING IN A SCREW MACHINE

This application is a continuation-in-part of application Ser. No. 08/511,055 filed on Aug. 3, 1995, now U.S. Pat. No. 5,670,112, and a continuation-in-part of application Ser. No. 08/393,200 filed Feb. 23, 1995, now abandoned.

BACKGROUND OF THE INVENTION

1. Field of the Invention

This invention relates to plastic processing machines, and more particularly to moveable screw arrangements for extrusion and injection molding.

2. Prior Art

The present invention relates to an apparatus for molding products from a plastic material, this Application being a Continuation - In - Part Application of U.S. patent application Ser. No. 08/511,055, filed Aug. 3, 1995, now U.S. Pat. No. 5,670,112, which is a Continuation - In - Part Application of U.S. application Ser. No. 08/393,200, filed Feb. 23, 1995, now abandoned, each of which are incorporated herein by reference.

Injection molding and extrusion employs the steps of hot working a plasticized or melted thermoplastic material and forcing same under high pressure into a mold or mold space, then allowing the material to cool sufficiently so that it hardens to the extent that it can retain its shape after removal from the mold or as it emanates from the mold.

During the plasticating process, it is often desirable to add a further processed material with the plastic material being worked within a screw housing. It is further desired to be able to add a solid, such as a pellet, wire, gas or a vapor, into the actual plastic material being molded or extruded.

Limitations of present plasticating screw machinery prevent the simultaneous introduction of a gas and/or a liquid, and or a vapor, and/or a solid, into that thermoplastic material as it is going into a mold or die.

It is therefore an object of the present invention, to provide a plasticating screw machine having capabilities not found in the prior art.

It is a further object of the present invention, to provide a screw machine which is able to present a solid and/or a liquid, and/or a vapor, and/or a gas, simultaneously or sequentially into a plastic being molded and/or extruded.

It is yet a further object of the present invention, to provide an arrangement which permits the rapid cooling and completion of a plastic part in a manner not found in the prior art.

It is yet still a further object of the present invention, to provide an extrusion and/or injection molding screw with multiple capabilities to mix and/or extrude and/or mold multiple components therewith in a manner not found in the prior art.

BRIEF SUMMARY OF THE INVENTION

The present invention relates to a plasticating screw machine for treating thermoplastic material and pressurizably directing that thermoplastic material into an extrusion die or into an injection mold.

The plasticating screw machine of the present invention comprises an external barrel shaped housing having an elongated screw shaft rotatively supported therewithin. The housing and the screw shaft have a proximal or first end and a distal or a second end. The screw shaft is rotatively empowered at the proximal first end of the housing by a motor drive means thereattached. At least one material in-feed supply hopper may be arranged through the housing near the proximal end thereof.

The screw shaft has a bore extending completely therethrough along its longitudinal axis, from its proximalmost end to its distalmost end. The bore has a wall surface which may be rifled, that is, has a spiral groove cut within its surface, to define a material moving path.

A non-rotational sleeve support may be arranged within the bore of the screw shaft, extending preferably from the proximal end of the housing, to the distal end of the shaft. A plurality of conduits may arranged within the sleeve support within the bore of the screw shaft. The conduits preferably extend out from the proximal end of the sleeve support, the conduits being in communication with any medium(s) such as a gas source, a vapor source, a liquid source, a or powder or solid source for feeding wire, pellets, powder, cooling fluid or the like into those conduits. The conduits have a distalmost end within the distal end of the screw shaft. The conduits may be held within a support baffle at the distal end of the sleeve. The sleeve support may be held in a bearing arranged within the walls of the bore of the screw shaft adjacent its distal end, for supportive carrying therein.

Each of the conduits may be moved longitudinally with respect to the screw shaft and or the sleeve support within the bore to advance its respective discharge end into any thermoplastic material as it emanates from the distal end of the housing. One or more of the conduits may be longitudinally advanceable through a die at the end of the housing, or into a injection mold at the distal end of the housing. The sleeve support may comprise a tubular member which encircles the conduit(s).

In a further preferred embodiment of the present invention, the entire sleeve support arrangement within the bore of the screw shaft may be longitudinally advanceable through the distal end of the housing, so as to present the delivery of any combination of medium(s) such as fluids, gas, vapors, and or solids such as wires, reinforcement fibers, optical glass and/or plastic at any location in or downstream of the plasticating screw and/or within the plastic being processed during the plasticating operation. Such medium(s) may permit the cooling, reinforcement, electrifying, lighting, softening, hardening, gasifying, hollowing or densification of any plastic being extruded or injected from the plasticating screw machine.

A further preferred embodiment contemplates a transfer of melted or fluid material along the annular path between the non rotatable sleeve support and the rifled wall of the bore within the screw shaft, to provide yet a further annular mixing chamber to the plasticating chamber between the flights of the elongated screw and the inner walls of the housing enclosing and supporting the elongated screw shaft.

A yet further preferred embodiment of the present invention contemplates the sleeve being rotatively disposed within the bore of the elongated screw shaft, either in a rotating or counter-rotating manner depending upon the direction of rotation of the elongated screw shaft itself. Such a rotating sleeve, would have a drive mechanism at its proximal end, in conjunction with a longitudinal displacement mechanism for advancing and retracting the sleeve longitudinally within the bore of the screw shaft, in a manner to permit any conduit therewithin to deliver and/or withdraw any single or combination of medium completely through the elongated screw shaft and or plastic being extruded and/or ejected from said screw and into a mold at the distal end of the plasticating screw machine.

In still yet a further embodiment of the present invention, when the screw shaft and associated internal conduits therethrough, are used in an injection molding operation, a mold may be utilized having an "inarticle" pin therewithin. The inarticle pin may be utilized to further supply and/or evacuate gas or liquids and/or powder from the injection mold. The inarticle pin may be retractably arranged within the mold, by a piston mechanism, which will move the pin from the mold itself. A fluid supply and vacuum line is in communication with the hollow inarticle pin and is in communication with a supply and discharge source, to permit such injection mold with a supply and vacuum means thereat.

Thus there has been shown, a unique screw construction or an injection molding machine or a plastic extrusion machine, wherein that same screw has a plurality of function transfer means included therewith. The separate conduits may be utilized individually or in combination, to continuously or sequentially add or withdraw a medium such as a vapor, a gas, a liquid, a foam, or a solid, into a plasticated material going into of through a die of a mold. The multiple conduits may be utilized to duct rearwardly excess gas, or vapor, or foam or liquid, or cooling material from the bore of the elongated screw shaft and/or support sleeve and/or tubular member therethrough, or mold, in conjunction with an inarticle pin arrangement or by themselves. If the screw shaft were to be used in the plastic injection format, the screw itself could be longitudinally advanceable and retractable towards a mold form.

The invention thus comprises a plasticating machine for the working and forcing of plastic material into a mold, said machine including an elongated housing having a first or proximal end and a second or proximal end, an elongated screw shaft with a screw flight therearound, the screw shaft being rotatably supported in the elongated housing, for the working of plastic between the screw shaft and the elongated housing, at least one delivery conduit generally longitudinally arranged through the screw shaft, from a proximal end to a distal tip end thereof, the screw shaft arranged to be movable with respect to the screw shaft to permit delivery of a medium through the screw shaft to any plastic being driven from the machine. The medium may be any single or combination of components selected from the group comprising vapor, liquid, gas, powder or solid.

The delivery conduit is movable longitudinally with respect to the elongated screw shaft. The delivery conduit is supported within a conduit support within a bore through the elongated screw shaft. The delivery conduit has a supply duct arranged on its proximal end, to supply said medium to the conduit for distribution of the medium into any plastic being delivered to a mold adjacent the distal end of the screw shaft. The conduit support may enclose a plurality of conduits therein, for the supply of a plurality of mediums to any plastic being delivered to a mold adjacent said distal end of the screw shaft. Each of the conduits in the plurality of conduits may be arranged parallel to one another. Each of the conduits in the plurality of conduits may be arranged coaxial with one another. At least one of the conduits may be arranged to carry a vacuum, to return a medium from the distal end of the screw shaft to the proximal end thereof. The conduit support may comprise an elongated sleeve. The elongated sleeve may be movable with respect to the elongated screw shaft. The elongated screw shaft may include a central bore therethrough from a proximal end to a distal tip end thereof, which central bore may have a grooved rifling therethrough, to assist in the movement of any medium passing through the bore itself. At least on of the conduits may be arranged to carry a cooling fluid therethrough, so as to provide a temperature control to any medium traveling thereadjacent. The elongated screw shaft may be movable longitudinally with respect to the elongated housing in which it is supported, to allow injection of plastic material from the housing into a mold thereadjacent. The mold may comprise a hollow injection mold. The conduits may be longitudinally advanceable and retractable with respect to the mold, to permit a medium to be delivered and/or withdrawn from any plastic supplied to the mold.

The invention also comprises a method of supplying a plastic to a mold for the manufacture of a plastic part therefrom, including the steps of providing an elongated rotatable screw shaft within an elongated barrel housing, the housing having a mold adjacent a distal end thereof, arranging a longitudinally directed bore through the elongated screw shaft from a proximal end to a distal end thereof, fitting at least one delivery conduit through the bore, so as to permit a medium to be directed through the screw shaft to any plastic being delivered to the mold adjacent the distal end of the housing, and attaching a medium supply duct at the proximal end of the proximal end of the conduit to permit a medium to be delivered through the conduit through the screw shaft and to a plastic part being generated at the distal end of the housing. The method may include the step of moving the delivery conduit longitudinally with respect to the screw shaft, to permit controlled delivery of the longitudinal location of any medium with respect to the screw shaft and the mold thereadjacent. The method may include the step of arranging a plurality of conduits within the bore of the elongated screw shaft, to permit the delivery of a plurality of mediums therethrough, to allow any plastic driven from the housing to be mixed with and/or treated by the mediums. The method may include the step of supplying any medium to the proximal end of the conduits, selected from the group comprising: a vapor, a cooling gas, a heated gas, a liquid, an optical fiber, a reinforcing fiber, an electrical conductor, and electrical resistor.

BRIEF DESCRIPTION OF THE DRAWINGS

The objects and advantages of the present invention, will become more apparent, when viewed in conjunction with the following drawings, in which.

DESCRIPTION OF THE PREFERRED EMBODIMENTS

Figure 1:
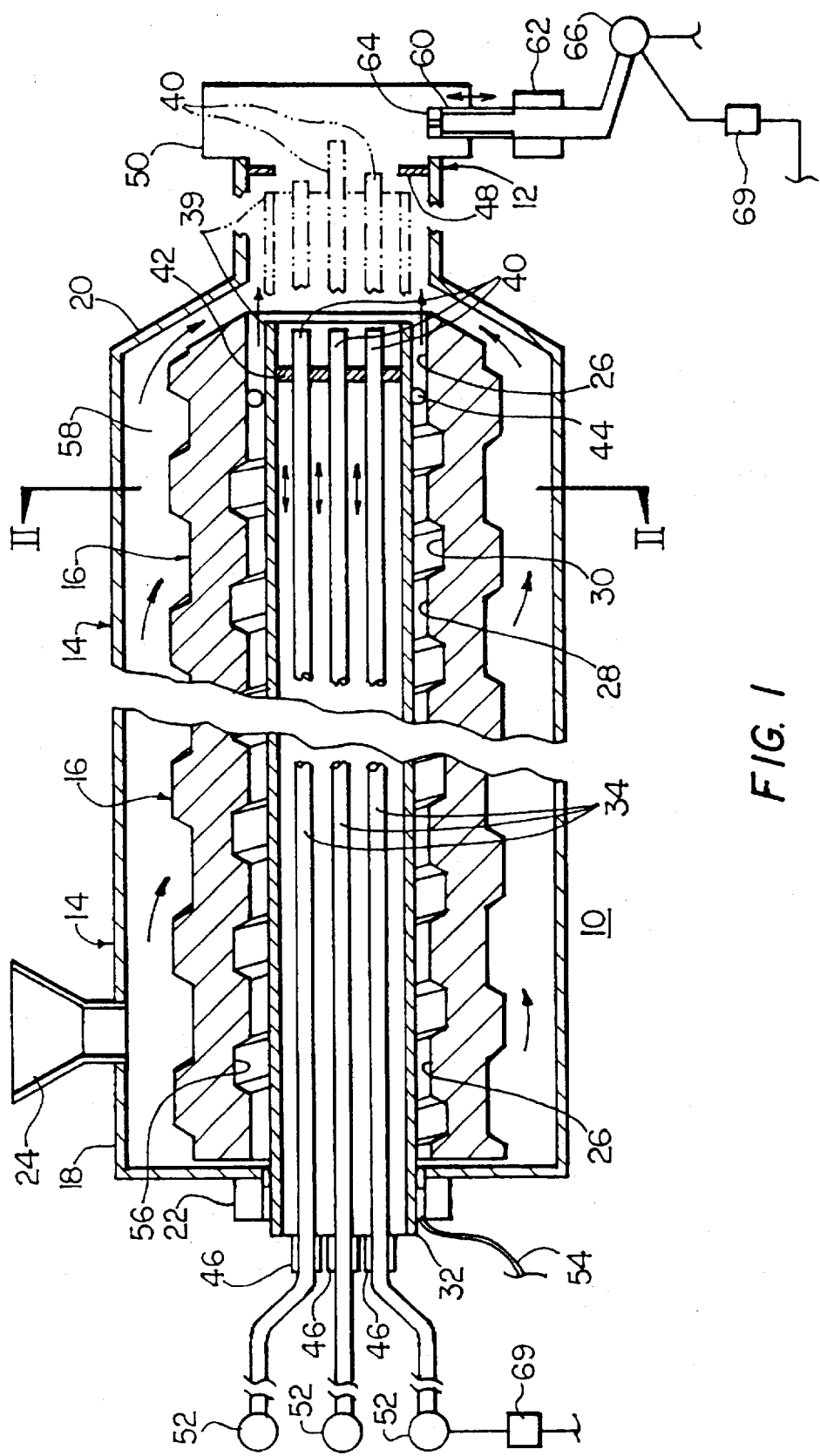
FIG. 1 is a side elevational view, in section, showing a plasticating screw shaft and multiple conduit assembly therewithin for treatment of thermoplastic material, according to the principles of the present invention.
Figure 2:
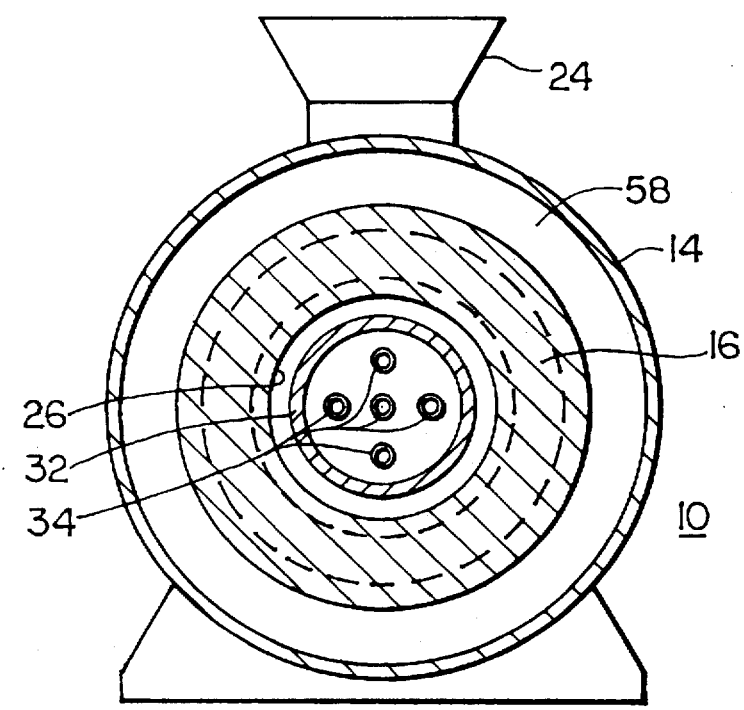
FIG. 2 is a view taken along the lines 2—2 of FIG. 1.

Referring now to the drawings in detail, and particularly to FIGS. 1 and 2, there is shown the present invention which relates to a plasticating screw machine 10 for treating of thermoplastic material and pressurizably directing that thermoplastic material into an extrusion die or into an injection mold 12 thereadjacent.

The plasticating screw machine 10 of the present invention comprises an external barrel shaped housing 14 having an elongated screw shaft 16 rotatively supported therewithin. The housing 14 and the screw shaft 16 have a proximal or first end 18 and a distal or a second end 20. The screw shaft 16 is rotatively empowered at the proximal first end 18 of the housing, 14 by a motor drive means 22 thereattached. At least one material in-feed supply hopper 24 may be arranged through the housing 14 near the proximal end 18 thereof.

The screw shaft 16 has a bore 26 extending completely therethrough along its longitudinal axis, from its proximal-most end to its distalmost end. The bore 26 has a wall surface 28 which may be rifled, that is, has a spiral groove 30 cut within its surface, to define a further material moving path.

A non-rotational sleeve support 32 may be arranged within the bore 26 of the screw shaft 16, extending preferably from the proximal end 18 of the housing 14, to the distal end 20 of the screw shaft 16. A plurality of conduits 34 may arranged within the sleeve support 32 within the bore 26 of the screw shaft 16. The conduits 34 preferably extend outwardly from the proximal end of the sleeve support 32, the conduits 34 being in communication with any medium(s) such as a gas source, a vapor source, a liquid source, a powder or solid source (for feeding wire, pellets, powder, an optical cable, an electrical conductor, an electrical resistance device or the like), cooling or heating fluid or the like into those conduits 34. The conduits 34 have a distalmost end 40 within the distal end 20 of the screw shaft 16. The conduits 34 may be held within a support baffle 42 at the distal end of the sleeve support 32. The sleeve support 32 may be held in a bearing 44 arranged within the walls 28 of the bore 26 of the screw shaft 16 adjacent its distal end, for supportive carrying therein.

Each of the conduits 34 may also be moved longitudinally with respect to the screw shaft 16 by a displacement gear 46 or the like, and or moving the entire sleeve support 32 within the bore 26 to advance its respective discharge end 39 into any thermoplastic material as it emanates from the distal end 20 of the housing 14. One or more of the conduits 34 may be longitudinally advanceable through a die 48 at the downstream end of the housing 14, or into an injection mold 50 at the distal end of the housing 14, the molds 48 and 50 (shown together for exemplary purposed). The sleeve support 32 may comprise a tubular member which completely longitudinally encircles the conduit(s).

In a further preferred embodiment of the present invention, the entire sleeve support 32 within the bore 26 of the screw shaft 16 may be longitudinally advanceable through the distal end 20 of the housing 14, so as to present the delivery of any combination of medium(s) such as fluids, gas, vapors, and or solids such as wires, reinforcement fibers (fiber glass), optical glass and/or plastic from a source 52 at the proximal end of the machine 10, so as to provide medium(s) at any location in or downstream of the plasticating screw 16 and/or within the plastic being processed during the plasticating operation. Such medium(s) may permit the cooling, reinforcement, electrifying, lighting, softening, hardening, gasifying, hollowing or densification of any plastic being extruded or injected from the plasticating screw machine 10.

A further preferred embodiment contemplates a transfer of melted or fluid material from a source 54, along the annular path 56 between the non-rotatable sleeve support 32 and the rifled wall 28 of the bore 26 within the screw shaft 16, to provide yet a further annular mixing, chamber in addition to the plasticating chamber 58 between the flights of the elongated screw shaft 16 and the inner walls of the housing 14 enclosing and supporting the elongated screw shaft 16.

A yet further preferred embodiment of the present invention contemplates the support sleeve 32 being rotatively disposed within the bore 26 of the elongated screw shaft 16, either in a rotating or counter-rotating manner depending upon the direction of rotation of the elongated screw shaft 16 itself. Such a rotating sleeve 32, would have a drive mechanism (not shown for simplicity of figures), at its proximal end, in conjunction with a longitudinal displacement mechanism (also not shown for simplicity of figures) for advancing and retracting the sleeve 32 longitudinally within the bore 26 of the screw shaft 16, in a manner to permit any conduit 34 therewithin to deliver and/or withdraw any single or combination of medium completely through the elongated screw shaft 16, and or plastic being extruded and/or ejected from said screw shaft 16 and into a mold 12 at the distal end of the plasticating screw machine 10.

In still yet a further embodiment of the present invention, when the screw shaft 16 and associated internal conduits 34 therethrough, are used in an injection molding operation, the injection mold 50 may be utilized having an "inarticle" pin 60 therewithin. The inarticle pin 60 may be utilized to further supply and/or evacuate gas or liquids and/or powder from the injection mold 50. The inarticle pin 60 may be retractably arranged within the mold 50, by a piston or like mechanism 62, which will move the pin 60 into and from the mold 50 itself. The pin 60 may have a jeweled orifice 64 at its inner end to minimize wear and hence prolong the life of such a pin 60. A fluid supply and vacuum line 66 is in communication with the hollow inarticle pin 60 and is in communication with the supply and discharge source 66, to permit such injection mold 50 with a supply and vacuum means thereat.

Thus there has been shown, a unique screw construction or an injection molding machine or a plastic extrusion machine, wherein that same screw has a plurality of function transfer means included therewith. The separate conduits may be utilized individually or in combination, to continuously or sequentially add or withdraw a medium such as a vapor, a gas, a liquid, a foam, or a solid, into a plasticated material going into or through a die or a mold. The multiple conduits may be utilized to duct rearwardly excess gas, or vapor, or foam or liquid, or cooling material from the bore of the elongated screw shaft and/or support sleeve and/or tubular member therethrough, or mold, in conjunction with an inarticle pin arrangement or by themselves, which may all be regulated by a control circuit 69 communicating with the conduit and sleeve moving apparatus, the medium sources and the pin for regulating quantity, temperature, pressure and distance. If the screw shaft were to be used in the plastic injection format, the screw itself could be longitudinally advanceable and retractable towards a mold form.

We claim:

1. A method of injecting a plastic into a mold for the manufacture of a plastic part therefrom, comprising the steps of:

providing an elongated rotatable screw shaft within an elongated barrel housing;

arranging a longitudinally directed bore through said elongated screw shaft from a proximal location therein, to a distal tip end thereof;

providing at least one longitudinally movable delivery conduit in said bore of said screw shaft, said delivery conduit being longitudinally movable with respect to said screw shaft, so as to permit a medium to be directed through said delivery conduit in said screw shaft to or from said proximal location in said screw shaft into or from the plastic downstream of said distal end of said screw shaft;

supplying a medium to said proximal location of said conduit to permit said medium to be delivered by said conduit in said screw shaft and into said plastic at said distal end of said screw shaft, said medium being supplied to or withdrawn from said conduit being selected from the group consisting of: a vapor, a cooling gas, a heated gas, a liquid, a solid material, a plastic material, a powder material, a reinforcing fiber, an electrical conductor, and an electrical resistor;

introducing said plastic between the barrel housing and said screw shaft;

rotating said screw shaft to plasticate said plastic and injecting said plasticated plastic into said mold;

moving said delivery conduit longitudinally with respect to said screw shaft; and directing at least one of said mediums through said delivery conduit to permit controlled delivery and/or withdrawal of one or more of said mediums therethrough to allow said infected plastic to be treated by at least one of said mediums.

2. The method as recited in claim 1, including the step of:

placing an inarticle pin into said mold to supply or evacuate a medium therefrom, said inarticle in having, a conduit arranged therewith to provide such supply or evacuation process thereto.

3. The method as recited in claim 2, including the step of:

controlling the timing of the supply of a medium to, or evacuation of a medium from said mold by said inarticle pin by a control circuit connected therewith.

* * * * *